(12) United States Patent
Warner et al.

(10) Patent No.: US 11,413,055 B2
(45) Date of Patent: Aug. 16, 2022

(54) MICROANCHORS FOR ANCHORING DEVICES TO BODY TISSUES

(71) Applicant: W. L. Gore & Associates, Inc., Newark, DE (US)

(72) Inventors: Clifford P. Warner, West Chester, PA (US); Sherif A. Eskaros, Elkton, MD (US); Kenneth Mazich, Birmingham, MI (US)

(73) Assignee: W. L. Gore & Associates, Inc., Newark, DE (US)

( * ) Notice: Subject to any disclaimer, the term of this patent is extended or adjusted under 35 U.S.C. 154(b) by 205 days.

(21) Appl. No.: 16/271,253

(22) Filed: Feb. 8, 2019

(65) Prior Publication Data
US 2019/0343541 A1 Nov. 14, 2019

Related U.S. Application Data

(63) Continuation of application No. 13/961,367, filed on Aug. 7, 2013, now Pat. No. 10,226,270.

(60) Provisional application No. 61/681,673, filed on Aug. 10, 2012.

(51) Int. Cl.
| | |
|---|---|
| *A61B 17/30* | (2006.01) |
| *A61F 2/07* | (2013.01) |
| *A61F 2/04* | (2013.01) |
| *A61B 17/064* | (2006.01) |
| *A61B 17/00* | (2006.01) |

(52) U.S. Cl.
CPC .......... *A61B 17/30* (2013.01); *A61B 17/0644* (2013.01); *A61F 2/04* (2013.01); *A61F 2/07* (2013.01); *A61B 2017/00867* (2013.01); *A61B 2017/0641* (2013.01); *A61B 2017/0645* (2013.01); *A61F 2002/045* (2013.01); *A61F 2220/0016* (2013.01)

(58) Field of Classification Search
None
See application file for complete search history.

(56) References Cited

U.S. PATENT DOCUMENTS

| | | | |
|---|---|---|---|
| 5,074,870 A | 12/1991 | Von Zeppelin | |
| 5,242,457 A * | 9/1993 | Akopov | A61B 17/064 |
| | | | 227/175.1 |
| 5,695,504 A | 12/1997 | Gifford, III et al. | |
| 5,843,167 A | 12/1998 | Dwyer et al. | |
| 5,944,750 A * | 8/1999 | Tanner | A61B 17/068 |
| | | | 606/108 |

(Continued)

FOREIGN PATENT DOCUMENTS

| | | |
|---|---|---|
| CN | 101453957 | 6/2009 |
| CN | 102307542 | 1/2012 |

(Continued)

OTHER PUBLICATIONS

Extended European Search Report from Application No. EP13827736.3, dated Jun. 16, 2015, 14 pages.

(Continued)

*Primary Examiner* — Shaun L David (57) ABSTRACT

Tissue anchoring devices in the form of microanchors that partially penetrate tissue, thereby avoiding full thickness penetration of the tissue, yet are secure enough to enable reliable device fixation and easy removal of the device while maintaining normal GI tract functions.

22 Claims, 13 Drawing Sheets

(56) References Cited

U.S. PATENT DOCUMENTS

| | | | |
|---|---|---|---|
| 5,972,022 A | 10/1999 | Huxel | |
| 6,846,296 B1 | 1/2005 | Milbocker et al. | |
| 6,981,983 B1* | 1/2006 | Rosenblatt | A61B 17/0401 128/898 |
| 7,056,286 B2 | 6/2006 | Ravenscroft et al. | |
| 7,111,627 B2 | 9/2006 | Stack et al. | |
| 7,326,231 B2* | 2/2008 | Phillips | A61B 17/064 606/153 |
| 7,736,377 B1 | 6/2010 | Anson et al. | |
| 8,202,311 B2 | 6/2012 | Demtriades et al. | |
| 8,585,836 B2 | 11/2013 | Carley et al. | |
| 10,226,270 B2 | 3/2019 | Warner et al. | |
| 2002/0032454 A1* | 3/2002 | Durgin | A61B 17/10 606/151 |
| 2002/0188318 A1 | 12/2002 | Carley et al. | |
| 2003/0033006 A1 | 2/2003 | Phillips | |
| 2004/0039414 A1 | 2/2004 | Carley et al. | |
| 2004/0044364 A1 | 3/2004 | Devries et al. | |
| 2004/0093024 A1 | 5/2004 | Lousararian et al. | |
| 2004/0117004 A1 | 6/2004 | Osborne et al. | |
| 2005/0085923 A1 | 4/2005 | Levine et al. | |
| 2005/0273138 A1 | 12/2005 | To et al. | |
| 2006/0161139 A1 | 7/2006 | Levine et al. | |
| 2007/0005147 A1 | 1/2007 | Levine et al. | |
| 2007/0027526 A1 | 2/2007 | Demetriades et al. | |
| 2007/0100355 A1* | 5/2007 | Bonde | A61B 17/12181 606/108 |
| 2007/0112423 A1* | 5/2007 | Chu | A61F 2/2445 623/2.11 |
| 2008/0109019 A1* | 5/2008 | Tulleken | A61B 17/11 606/153 |
| 2008/0221599 A1* | 9/2008 | Starksen | A61B 17/00234 606/157 |
| 2008/0234705 A1* | 9/2008 | Cropper | A61B 17/1285 606/157 |
| 2008/0262596 A1* | 10/2008 | Xiao | A61B 17/12118 623/1.14 |
| 2009/0114233 A1* | 5/2009 | Edoga | A61B 17/072 128/898 |
| 2009/0171442 A1 | 7/2009 | Young et al. | |
| 2009/0182355 A1 | 7/2009 | Levine et al. | |
| 2009/0204129 A1* | 8/2009 | Fronio | A61F 13/36 606/151 |
| 2009/0259250 A1 | 10/2009 | Reydel | |
| 2010/0249920 A1 | 9/2010 | Bolling et al. | |
| 2010/0324584 A1 | 12/2010 | Shaw | |
| 2010/0331756 A1 | 12/2010 | Meage et al. | |
| 2011/0034953 A1 | 2/2011 | Milo | |
| 2011/0040368 A1 | 2/2011 | Petersen | |
| 2011/0087249 A1 | 4/2011 | Rodrigues et al. | |
| 2011/0093002 A1 | 4/2011 | Rucker et al. | |
| 2011/0276091 A1 | 11/2011 | Melanson | |
| 2012/0150224 A1 | 6/2012 | Bolotin | |
| 2012/0277853 A1* | 11/2012 | Rothstein | A61F 2/2466 623/2.11 |
| 2013/0053862 A1* | 2/2013 | Tulleken | A61B 17/11 606/108 |
| 2013/0289690 A1 | 10/2013 | Thapliyal | |
| 2014/0148849 A1* | 5/2014 | Serina | A61B 17/0401 606/232 |
| 2015/0273138 A1 | 11/2015 | Wolff et al. | |

FOREIGN PATENT DOCUMENTS

| | | | |
|---|---|---|---|
| EP | 1749484 | 3/2007 | |
| GB | 2472602 A | 2/2011 | |
| JP | 03-242138 A | 10/1991 | |
| JP | 08-299456 A | 11/1996 | |
| JP | 11-500642 A | 1/1999 | |
| JP | 2002-522107 A | 7/2002 | |
| JP | 2004-513670 A | 5/2004 | |
| JP | 2005-518239 A | 6/2005 | |
| JP | 2006-507910 A | 3/2006 | |
| JP | 2006-512157 A | 4/2006 | |
| JP | 2007-075596 A | 3/2007 | |
| JP | 2011-518017 A | 6/2011 | |
| WO | WO-1996025886 | 8/1996 | |
| WO | WO-2001041624 | 6/2001 | |
| WO | WO-2003020106 | 3/2003 | |
| WO | WO-2003020106 A2 | 3/2003 | |
| WO | WO-2003020106 A3 | 3/2003 | |
| WO | WO-2003071955 A2 | 6/2005 | |
| WO | WO-2004049982 | 3/2006 | |
| WO | WO-2008108936 | 9/2008 | |
| WO | WO-2008108936 A1 | 9/2008 | |
| WO | WO-2009085107 A1 | 7/2009 | |
| WO | WO-2010099437 | 9/2010 | |
| WO | WO-2010099437 A1 | 9/2010 | |
| WO | WO-2011021158 | 2/2011 | |
| WO | WO-2011021158 A2 | 2/2011 | |
| WO | WO-2011034973 | 3/2011 | |
| WO | WO-2009130631 | 6/2011 | |
| WO | WO-2012031204 | 3/2012 | |
| WO | WO-2012031204 A2 * | 3/2012 | A61B 17/0401 |
| WO | WO-2012058582 | 5/2012 | |

OTHER PUBLICATIONS

International Search Report and Written Opinion from PCT/US2013/054043, dated Nov. 8, 2013, 14 pages.
European Search Report and Search Opinion Received for EP Application No. 16199750.7, dated Mar. 1, 2017, 4 pages.
European Search Report and Search Opinion Received for EP Application No. 18171949.3, dated Jun. 18, 2018, 8 pages.

* cited by examiner

MICROANCHORS FOR ANCHORING DEVICES TO BODY TISSUES

CROSS REFERENCE TO RELATED APPLICATIONS

This application is a continuation of U.S. application Ser. No. 13/961,367, filed Aug. 7, 2013, which claims priority to U.S. Provisional Application No. 61/681,673, filed Aug. 10, 2012, both of which are incorporated herein by reference in their entireties for all purposes.

FIELD OF THE INVENTION

The present invention is directed to microanchors for anchoring devices to body tissues, and more particularly, to microanchoring devices that enable reliable device fixation and easy removal of the device, while maintaining normal gastrointestinal (GI) tract function.

BACKGROUND OF THE INVENTION

Implantable devices such as intestinal sleeves are known in the industry. A common difficulty associated with such devices that are designed for implantation in the GI tract is reliable anchoring of the devices. The GI tract is a very dynamic area of the body. There is much movement, flow, and other disruptive action that exerts forces on the implanted device. Anchoring the device so that it stays in place without migration in these dynamic locations is very difficult. The tissue anchors must be secure enough to anchor endolumenally delivered devices in the GI tract and yet produce minimal impact to normal physiological functions of the GI tract, such as motility, blood supply to the surrounding tissue, secretions, patency, etc.). In addition, the tissue anchors must avoid causing pain to the patient.

An even greater challenge is presented with temporary implantable devices—those that are designed to be anchored in the body for a limited period of time, and then removed. The tissue anchors for these devices must meet all of the same criteria for reliable fixation and allowing normal GI tract functions, but must also permit endolumenal removal of the device. A tissue anchor satisfying all of these needs is highly desirable.

SUMMARY OF THE INVENTION

The present invention provides tissue anchors in the form of microanchors, the length of which ensure penetration of only the submucosa of the tissue, yet are secure enough to enable reliable device fixation and easy removal of the device while maintaining normal GI tract functions. The invention includes several embodiments of these microanchors.

In a first embodiment, the present invention provides a microanchor comprising a first tissue engagement member, a second tissue engagement member, and a strain relieving connector joining the first tissue engagement member to the second tissue engagement member, wherein said device has a retracted state and an engaged state, the first tissue engagement member and said second tissue engagement member forming a pincer in the engaged state.

In another embodiment, the present invention provides a microanchor for fixating a device within a body lumen comprising a first portion attached to said device, a second portion having at least one tissue engagement member for insertion into a wall of the body lumen, and a reversibly deformable and recoverable segment located between the first portion and the second portion.

In a third embodiment, the present invention provides a microanchor comprising a central hub and at least three tissue engagement members radially oriented on the central hub, wherein the device has a constrained state and an engaged state, and wherein the tissue engagement members are in apposition to each other in the engaged state.

DETAILED DESCRIPTION OF THE INVENTION

Figure 1A:
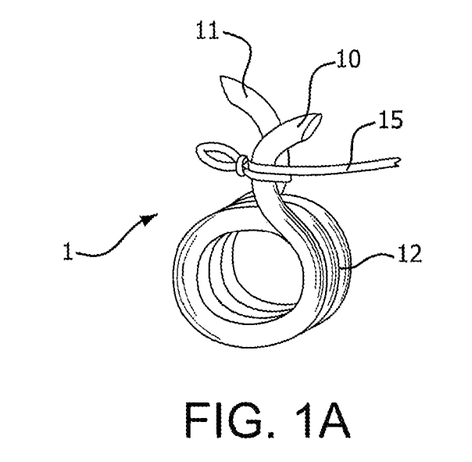
FIG. 1A is a perspective view of an exemplary embodiment of the invention in a retracted state.

The present invention will now be described with reference to exemplary embodiments. In a first embodiment illustrated in FIGS. 1A and 1B, a microanchor device 1 is illustrated having a first tissue engagement member 10 and second tissue engagement member 11 joined by a connector 12. Connector 12 in this embodiment is a coil spring made of a metal such as nitinol or stainless steel. Other biocompatible materials may also be used provided that they can be repeatedly retracted and engaged as described herein including but not limited to chrome cobalt alloys such as Elgiloy or L605 and titanium alloys such as Titanium Beta 3. FIG. 1A illustrates the microanchor device 1 in a retracted state. In this retracted state, first tissue engagement member 10 and second tissue engagement member 11 are physically wound against the tension of the spring such that they are in proximity to each other. The engagement members 10 and 11 are then physically constrained using external means such as a suture or ligament or line 15. Line 15 is tied around both engagement members 10 and 11 to physically constrain them in retracted state. The force of the spring coil connector 12 is stored as potential energy in this retracted state. It should be understood that the use of tethers to restrain tissue engagement members is merely exemplary and that any thermal or mechanical means to initially restrain tissue engagement members could be employed. In one embodiment, a rigid sheath could be employed to restrain tissue engagement members.

Figure 1B:
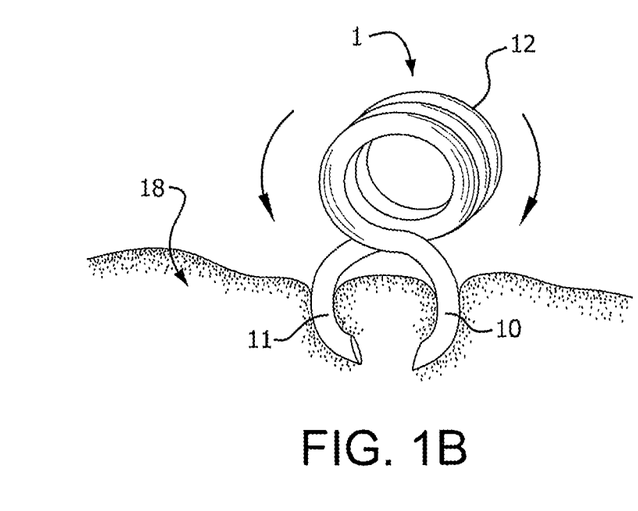
FIG. 1B is a perspective view of the microanchor of FIG. 1A in an engaged state.
Figure 1C:
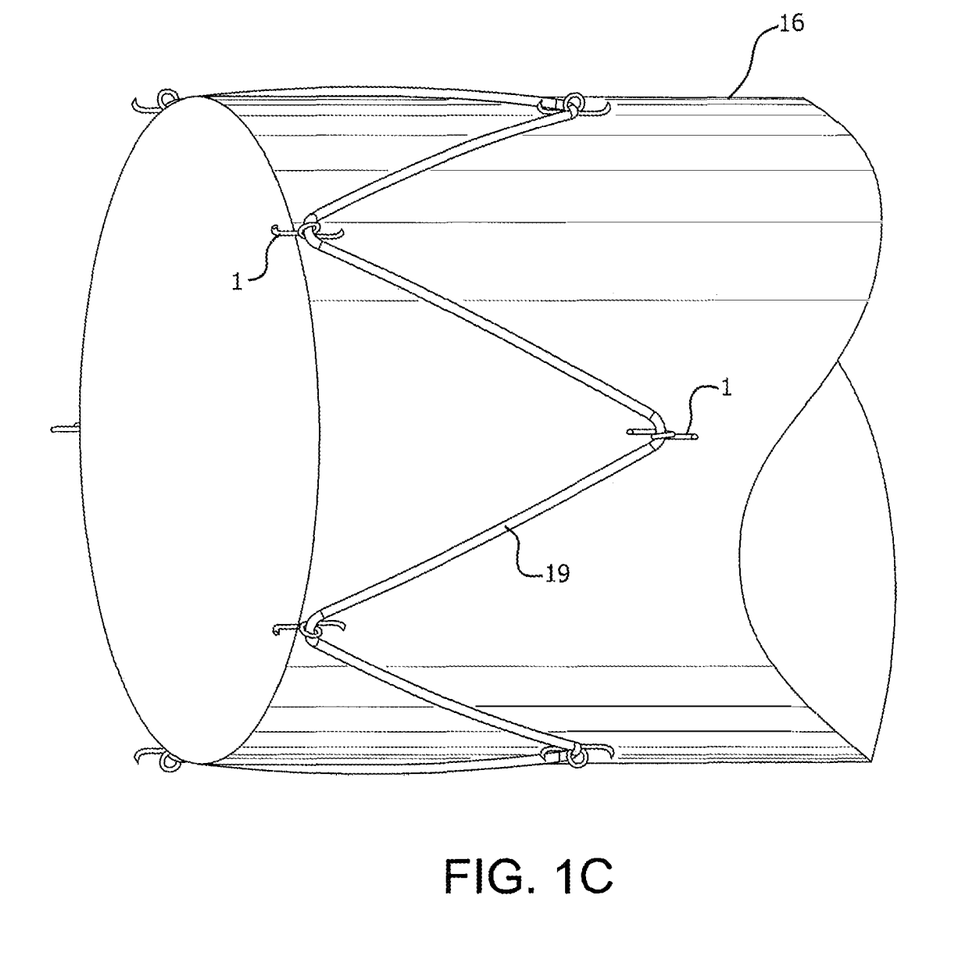
FIG. 1C is a perspective view of microanchors of FIG. 1A mounted on a stent graft attached to a graft.

In use, a plurality of microanchor devices 1 as illustrated in FIG. 1A are mounted around a portion of a device to be anchored within the body. For example, as illustrated in FIG. 1C, microanchor devices 1 are mounted at various locations on a stent frame 19 of a device to be anchored within a body. As illustrated in FIG. 1C, microanchor devices 1 are mounted at the apices of the stent frame and are depicted in their restrained state. The stent frame is optionally used in combination with a graft member 16 which may extend any desired length, including beyond the stent frame 19.

For insertion into a body, the stent frame 19 and any associated graft 16 are diametrically compressed into a small configuration suitable for insertion into a catheter device, for example. The stent frame 19 and any associated graft 16 are then advanced along the catheter to the desired point of deployment within the body. At that point, the stent frame 19 and any associated graft 16 are deployed from the catheter and expand to the desired diametrical size to engage the tissue or vessel walls.

After deployment of stent, the operator, typically a doctor, will manipulate tether lines 15 (as shown in FIG. 1A), which will in turn release first tissue engagement member 10, and second tissue engagement member 11. At that point, as illustrated in FIG. 1B, microanchor device 1 releases the stored potential energy within connector 12 and forces first tissue engagement member 10 and second tissue engagement member 11 into an engaged state, illustrated in FIG. 1B. In this engaged state, first tissue engagement member 10 and second tissue engagement member 11 form a pincer. By "pincer" as used herein is meant a configuration in which first tissue engagement member 10 and second tissue engagement member 11 are essentially two grasping jaws working on a pivot used for gripping tissue 18.

With reference again to FIG. 1C, once all of the microanchor devices 1 have been deployed from their retracted state to their engaged state, the stent frame 19 and any associated graft 16 are anchored securely to the body tissue. Although this anchoring is secured, it is not necessarily permanent. Microanchor device 1 is designed to penetrate only the sub-mucosa of the tissue. The microanchors described herein, typically penetrate less than one millimeter into the tissue. As a result, with the application of appropriate force in the appropriate direction, microanchor device 1 can be disengaged or removed from the tissue 18. In this way, the stent frame 19 and any associated graft 16 can be removed from the body after disengaging microanchor devices 1.

Figure 1D:
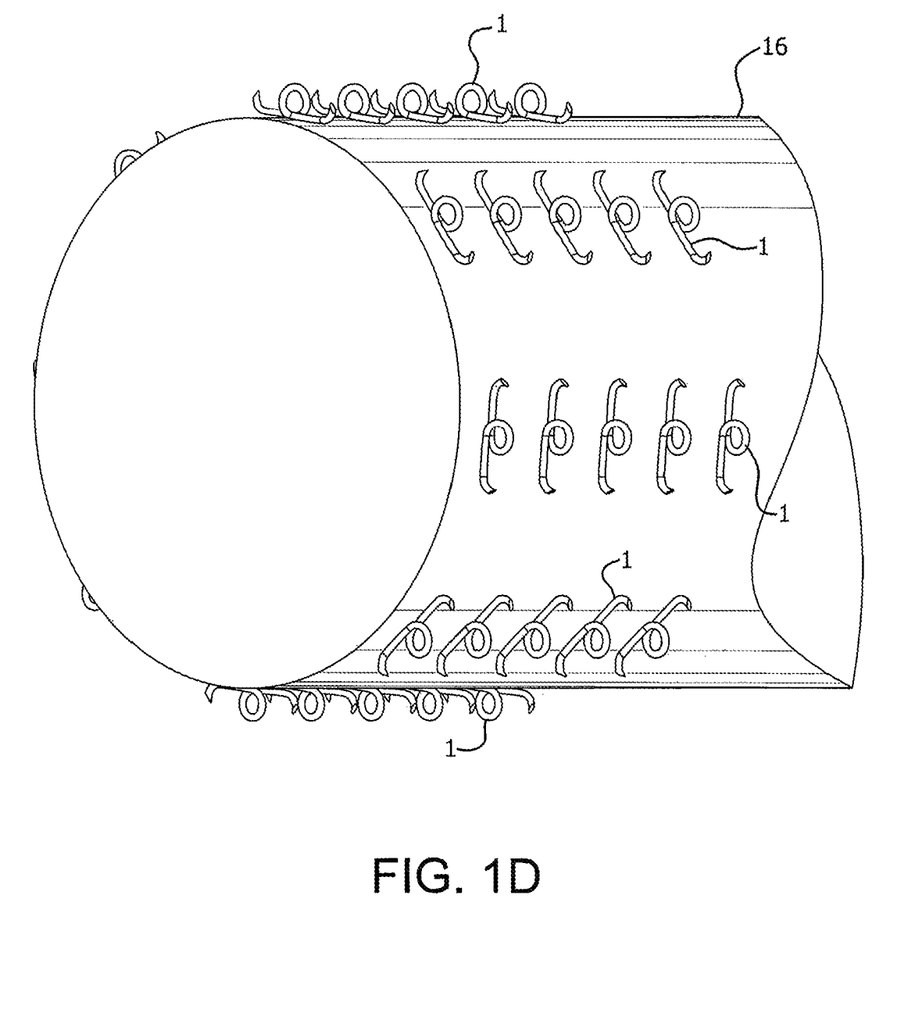
FIG. 1D is a perspective view of microanchors of FIG. 1A mounted on a sleeve.

An alternate device configuration is illustrated in FIG. 1D where a plurality of microanchor devices 1 as illustrated in FIG. 1A are mounted at various locations of a sleeve device 16 to be anchored within a body without the use of a stent. As illustrated in FIG. 1D, microanchor devices 1 are mounted directly on graft member 16 and are depicted in their restrained state. The anchoring devices 1 may mounted on a portion of the graft, such as the proximal length of the graft, or may mounted throughout the length of the graft (figure not shown). The microanchors could be attached individually to the sleeve and oriented in parallel to resist distal movement of the sleeve. Alternatively, the anchors could be randomly oriented. In another embodiment, the microanchors could be attached to one another to form a chain which is subsequently attached to the sleeve.

The device shown in FIG. 1D may be packed into a small configuration suitable for insertion into a catheter device. For deployment the packed device may be advanced along the catheter to the desired point of deployment within the body. After deployment the tissue engagement members on graft 16 may be put in the proximity of the tissue, through a tissue approximation mechanism. An example of the tissue approximation mechanism is use of an inflating balloon to put graft 16 and the microanchor device 1 in proximity of the tissue that it will engage.

After approximating the microanchor device 1 to the tissue, the operator, typically a doctor, will manipulate tether lines 15, which will in turn release first tissue engagement member 10, and second tissue engagement member 11, by releasing (as illustrated in FIG. 1B) the stored potential energy within connector 12 and forming the pincer as described earlier to engage the tissue.

Figure 2A:
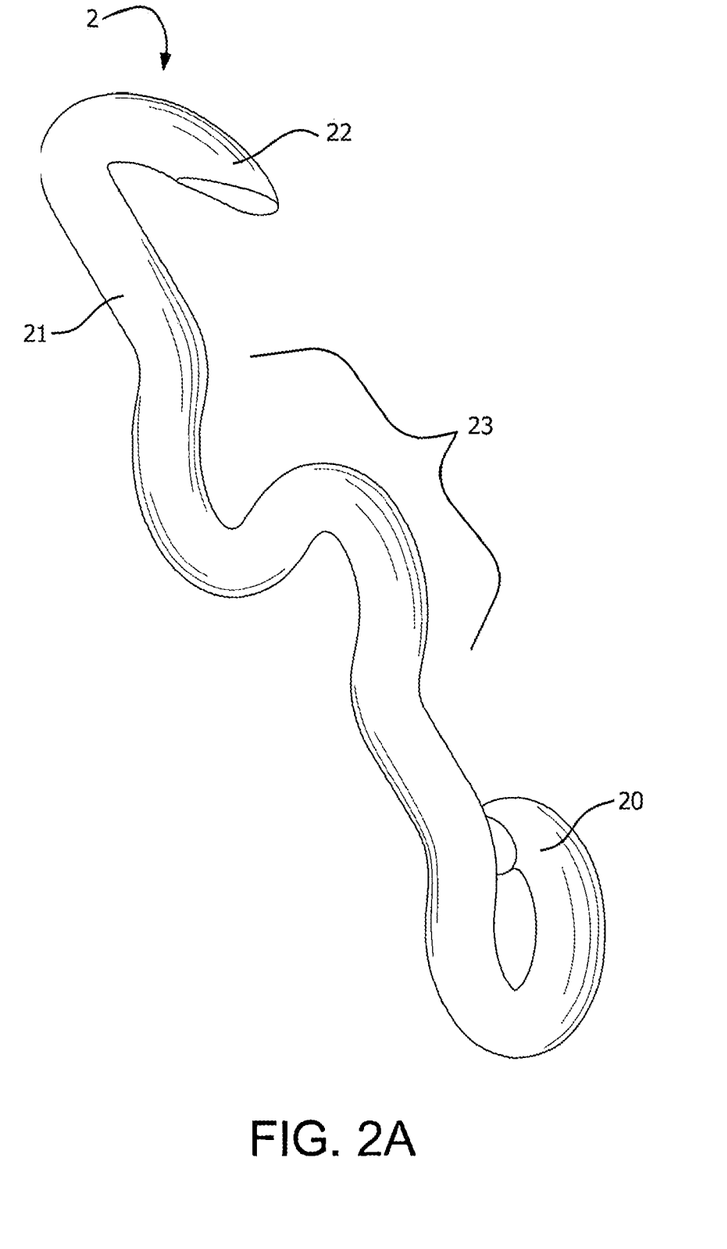
FIG. 2A is a perspective view of another exemplary embodiment of the present invention.

A second embodiment of the present invention is illustrated in FIG. 2A. In FIG. 2A, a microanchor device 2 is shown. The microanchor device 2 has a first portion 20, a second portion 21, and a connector portion 23 connecting the first portion 20 to the second portion 21. The first portion 20 is adapted for attachment to an apparatus to be anchored within the body. The second portion 21 of the microanchor device 2 has a tissue engagement member 22 adapted for insertion into body tissue. The tissue engagement member 22 may be a microanchor that is dimensioned to only extend into the submucosa of the tissue upon implantation and deployment of the microanchor device 2. The size of the tissue engagement member 22 is limited so that the anchoring member 22 does not extend through the wall of the tissue and so that upon removal the tissue engagement member does not tear the tissue.

The first portion 20 and second portion 21 of the microanchor device 2 are coupled together through a reversibly deformable or resilient connector portion 23. Upon implantation of the apparatus in a body, the tissue engagement member 22 is engaged with a body tissue and the first portion 20 is coupled to the apparatus. As the body exerts forces on the implanted apparatus, the apparatus may move in response to these external forces. The resilient or reversibly deformable portion 23 may provide a strain relief that may absorb these forces by stretching or deforming along the length of the deformable portion 23. The dissipation of the force should reduce the likelihood of the engagement member 22 disengaging from the tissue. The application of a force to the apparatus will cause connector segment 23 to stretch or deform, thus absorbing the shock or energy from the force without directly exerting that force through the tissue engagement member on the tissue itself.

In the embodiment illustrated in FIG. 2A, connector segment 23 is formed of the same wire as the rest of the microanchor device, which can be a material such as nitinol or stainless steel or other reversibly deformable (resilient) material. Connector segment 23 in the illustrated embodiment is shaped in the form of an "S". Upon application of a force to first portion 20, the "S" connector segment 23 straightens out or substantially straightens out (stretches or lengthens) to absorb the shock. The deformation of the "S" shape may reduce the amount of force that will transfer through the first portion 20 of the microanchor device 2 to the second portion 21 and the engagement member 22. The connector segment 23 absorbs the force in order to reduce the likelihood of tissue engagement member 22 pulling out of the tissue. Upon release of the force, connector segment 23 then reversibly regains its initial "S" shape, ready to deform again to absorb further forces on microanchor device 2. In this way, when a plurality of microanchor devices 2 of this embodiment are disposed around an apparatus anchored within a body, the microanchor devices 2 are able to absorb the repeated shock of forces applied to the device, such as within the intestine. The apparatus anchored within the intestine is thereby securely maintained.

As with the microanchor device illustrated in FIGS. 1A-1C, the tissue engagement member 22 of microanchor device 2 only penetrates the submucosa of the tissue. Therefore upon application of an appropriate force to tissue engagement member 22, it may be removed from the tissue, thereby allowing the apparatus to be removed from the body with minimal injury or tearing to the tissue wall.

Figure 2B:
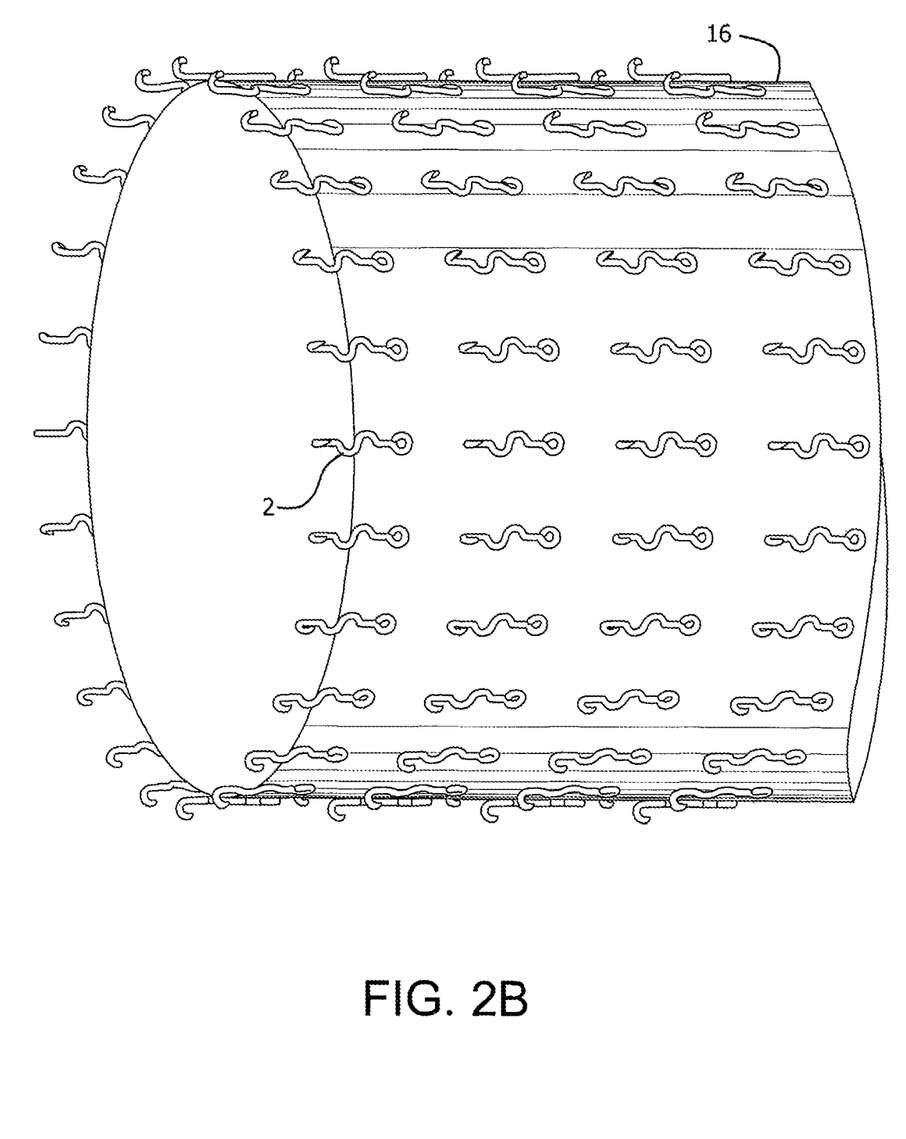
FIG. 2B is a perspective view of microanchors of FIG. 2A mounted on a sleeve

In use, a plurality of microanchor devices as illustrated in FIG. 2A can be mounted around a portion of a device to be anchored within the body. For example, as illustrated in FIG. 2B, a plurality of microanchor devices 2 are mounted at various locations of a sleeve device 16 to be anchored within a body without the use of a stent. The microanchors could be attached individually to the sleeve and oriented in parallel to resist distal movement of the sleeve. Alternatively, the anchors could be randomly oriented.

The device shown in FIG. 2B may be packed into a small configuration suitable for insertion into a catheter device. For deployment the packed device may be advanced along the catheter to the desired point of deployment within the body. After deployment, the tissue engagement members of microanchor devices 2 on graft 16 may be put in the proximity of the tissue, through a tissue approximation mechanism. An example of the tissue approximation mechanism is use of an inflating balloon to put graft 16 and the microanchor device 2 in proximity of the tissue that it will engage.

After approximating the microanchor device 2 to the tissue, the operator, typically a doctor, will manipulate the engagement members with the tissue by pulling on the catheter, which would set the engagement members into the tissue.

Figure 3A:
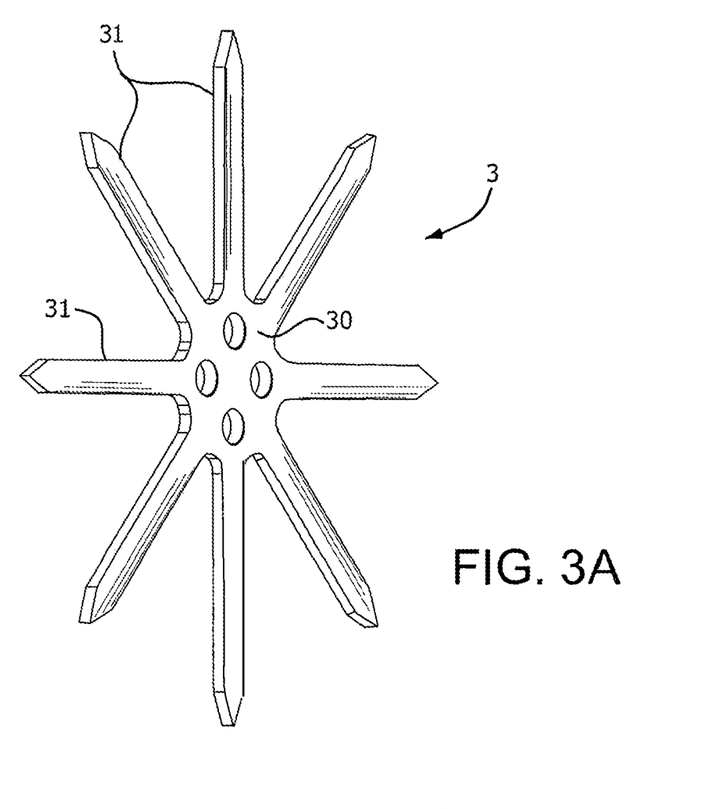
FIG. 3A is a perspective view of another exemplary embodiment of the present invention in a retracted state.
Figure 3B:
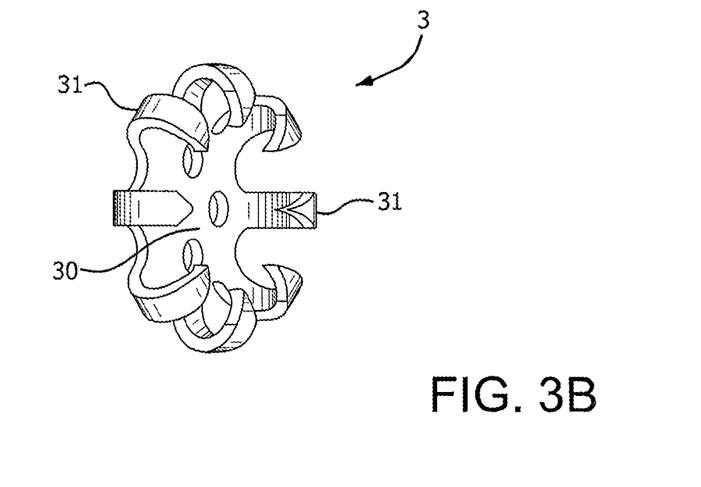
FIG. 3B is a perspective view of the microanchor of FIG. 3A in an engaged state.
Figure 3C:
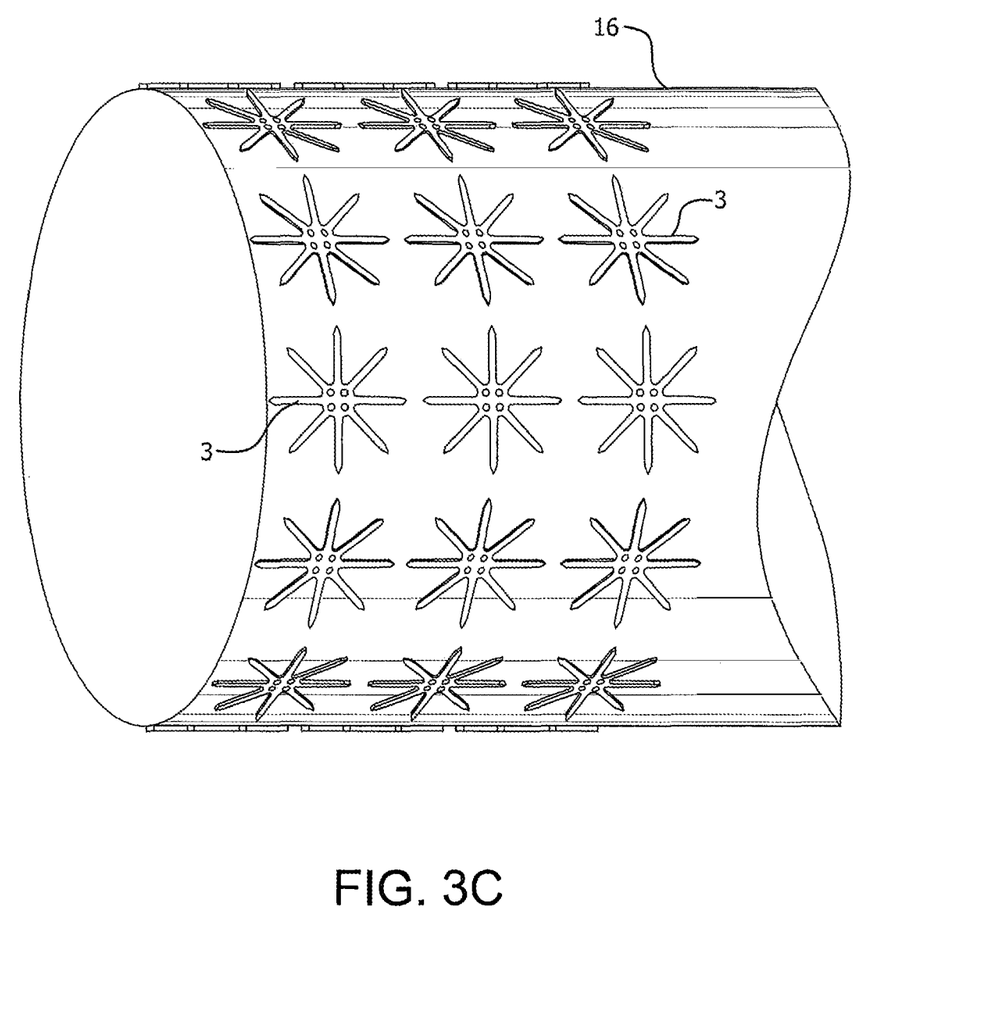
FIG. 3C is a perspective view of microanchors of FIG. 3A coupled to an implantable device.
Figure 3D:
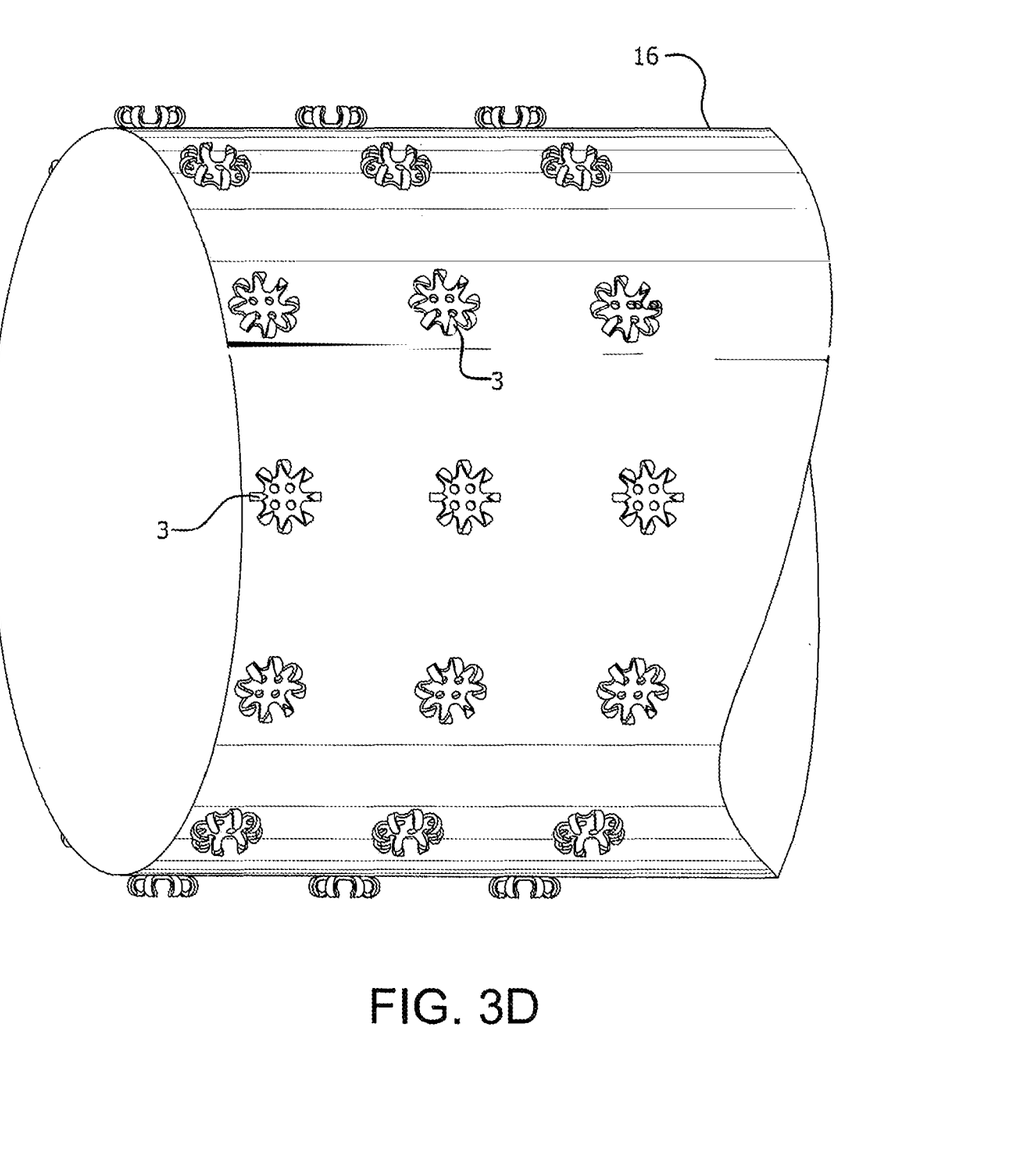
FIG. 3D is a perspective view of microanchors of FIG. 3A coupled to an implanted device in an engaged state.

Another embodiment of the present invention is illustrated in FIGS. 3A-3D. As shown in FIG. 3A, a microanchor device 3 has a central hub 30 and a plurality of tissue engagement members 31 extending therefrom. Typically this microanchor device 3 is formed of a shape memory material such as nitinol. The configuration illustrated in FIG. 3A depicts the device in a retracted state. A plurality of microanchor devices 3 may be mounted around an apparatus to be anchored within a body, such as around a stent frame of such device, as shown in FIGS. 3C & 3D. Upon insertion and deployment of the apparatus at the desired location within the body, microanchor device 3 is released from its retracted state into an engaged state, as illustrated in FIG. 3B. Typically, with shape memory metals, this release from retracted state to engaged state is stress induced, however, it is envisioned that this activation could be thermally induced as well. In an engaged state, tissue engagement members 31 are in apposition to each other. This means that they are facing substantially toward one another in a configuration that effectively grips the body tissue. As with the previous two embodiments, microanchor device 3 is adapted to only penetrate the submucosa, approximately one millimeter, in the tissue. As a result, upon application of suitable force, it can be removed from the tissue. Nonetheless, the apparatus anchored by the microanchor device 3 is securely maintained at its position within the body, enduring the forces and shock experienced by the apparatus, holding it securely in place. The multiple directions of the anchor members allow the device to withstand the forces that are within a body lumen. These forces may not be in a single direction and the multiple directions of the anchor members allow the device to be maintained within the lumen.

Turning now to FIGS. 3C and 3D, the microanchor device 3 is shown coupled to an implant. The microanchor device 3 may be coupled directly to an end of a tubular member in an evenly spaced distribution around the outside surface of the tubular member. In FIG. 3C the microanchor device is shown in a retracted state on the outside surface of a tubular member 16 and in FIG. 3D the microanchor device 3 is shown in an engaged state on the outside surface of the tubular member 16. The location of the anchoring devices 3 with respect to the tubular member or implanted device may be coupled together in any pattern.

In FIGS. 4A-4D, another alternative embodiment of the present invention is shown. The microanchor device 4 is similar to the embodiment of FIGS. 2A and 2B. The microanchor device 4 may have two tissue engaging portions 42. Each of the tissue engaging portions 42 may be coupled to a device engagement portion 44 with a connector portion 46 therebetween. The tissue engagement member 42 of the microanchor device 4 may allow the device to couple to a body tissue when implanted into a patient. The size and shape of the tissue engagement member 42 is designed to limit the depth of tissue wall penetration to the submucosa layer of the tissue wall. The limit on tissue penetration depth may allow the microanchor device 4 to be removed from the tissue wall and also limit any damage that may be caused by the tissue engagement member 42.

Figure 4A:
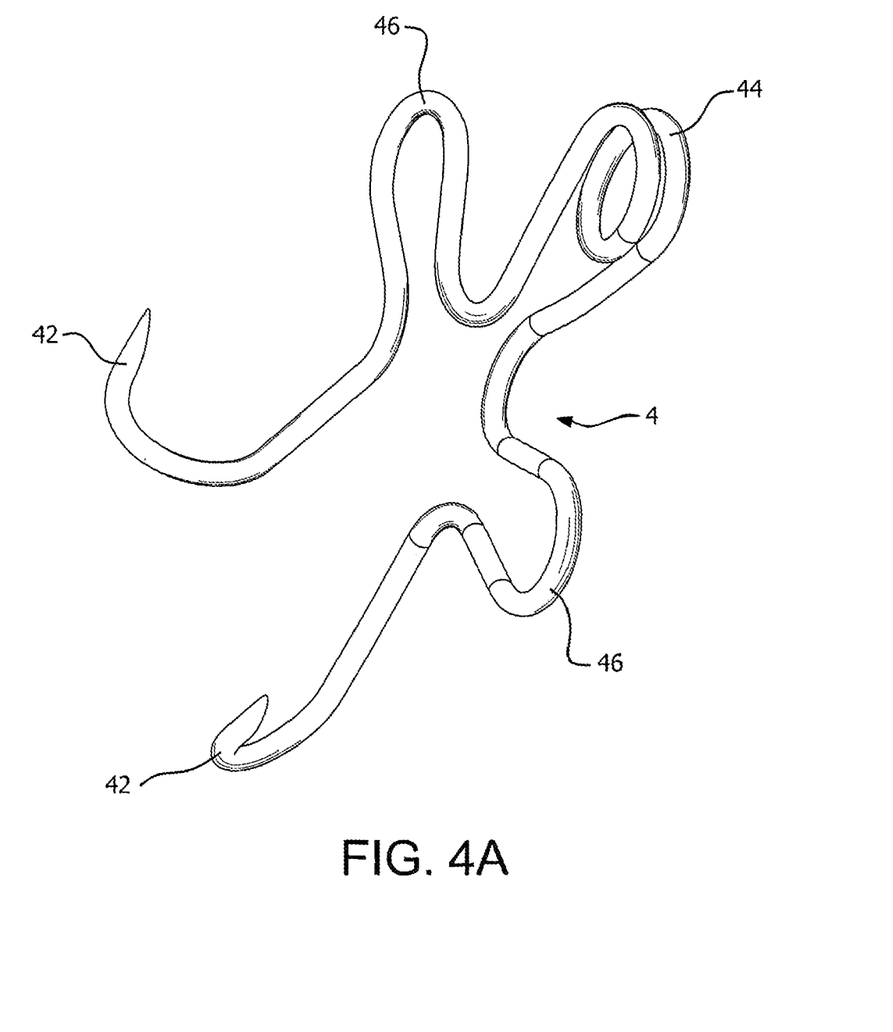
FIG. 4A is a perspective view of another exemplary embodiment of the present invention
Figure 4B:
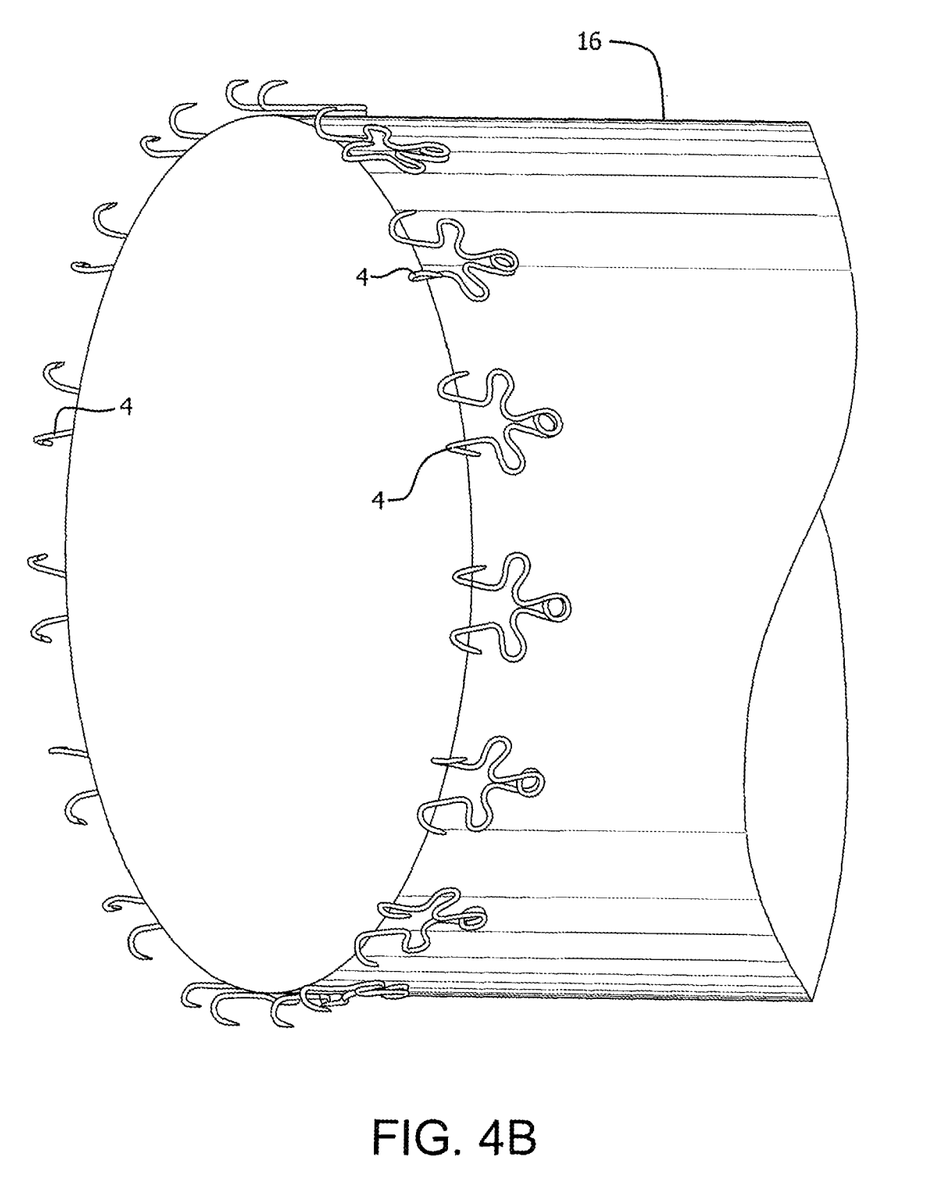
FIG. 4B is a perspective view of microanchors of FIG. 4A coupled to an end portion of an implantable sleeve device.
Figure 4C:
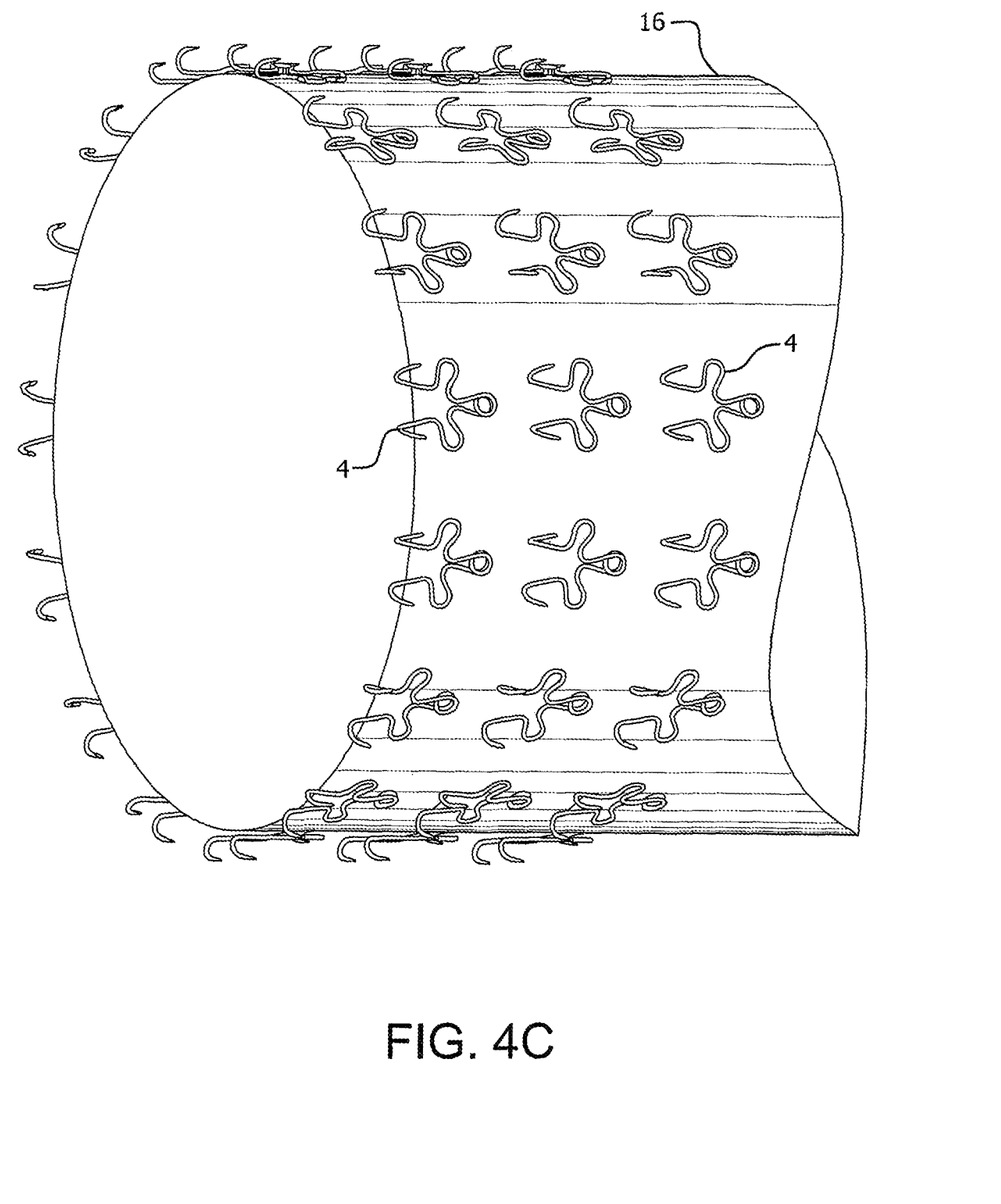
FIG. 4C is a perspective view of microanchors of FIG. 4A coupled to an end region of an implantable sleeve device.
Figure 4D:
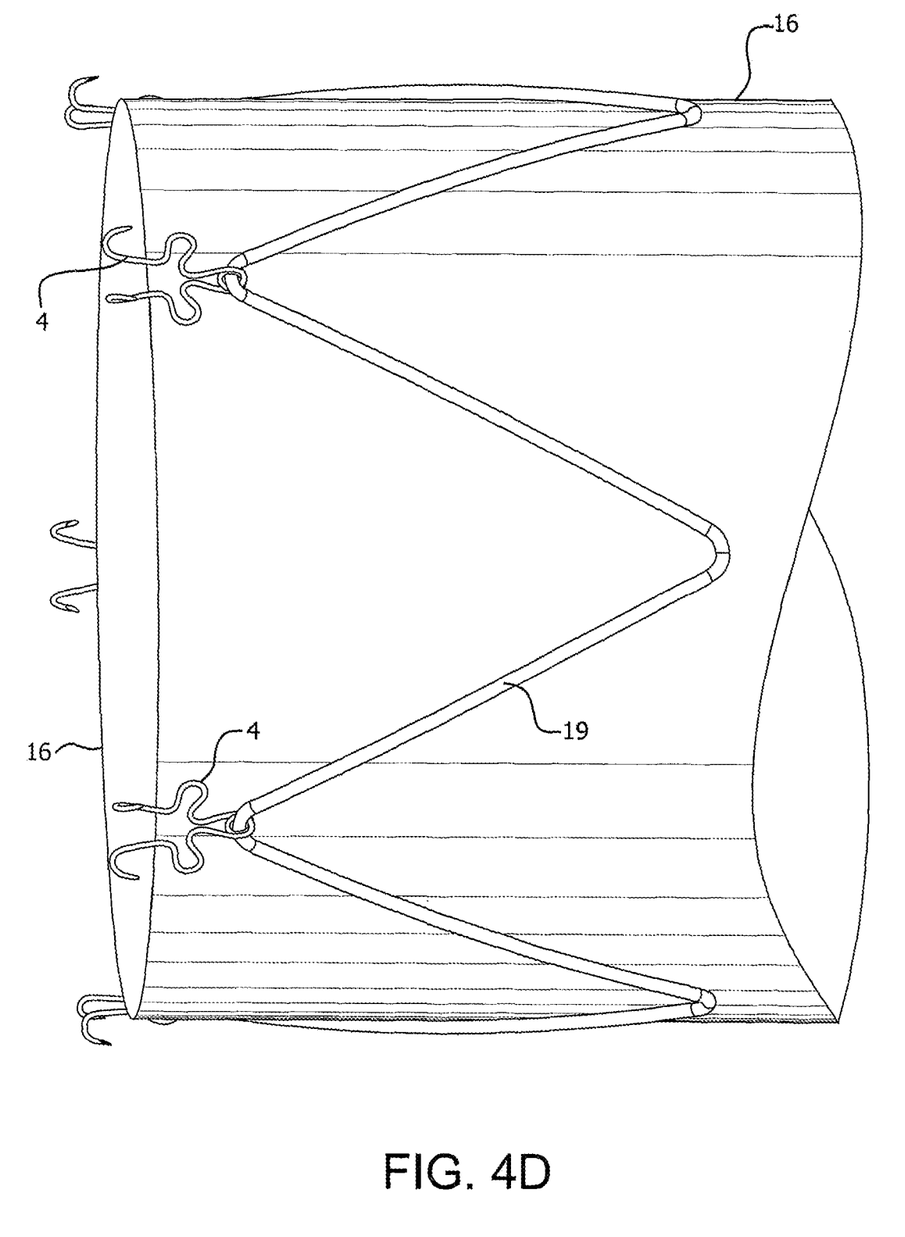
FIG. 4D is a perspective view of microanchors of FIG. 4A coupled to an implantable device comprising a stent portion and a graft portion.

The connector portions 46 may provide a strain relief when the microanchor device 4 is implanted into a body lumen. As forces from the body act upon a device (See FIGS. 4B-4D) coupled to the microanchor device 4, the connector portions 46 may stretch or deform in order to reduce the force that may be translated to the tissue engaging portions 42. The reduction of force on the tissue engagement portions 42 may prevent the tissue engagement portions from pulling out of the tissue wall and also may prevent an implanted device from migrating or moving from the implanted location. A device might consist of a sleeve device 16 as shown in FIGS. 4B and 4C, or a stent frame 19 in combination with a sleeve device 16 as shown in FIG. 4D. Including multiple microanchor devices 4 on an implantable device may further reduce the likelihood of a device from being removed prematurely from an implant site.

Figure 5:
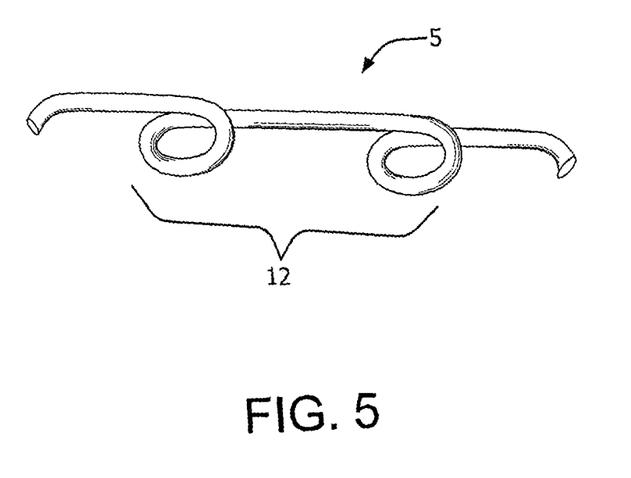
FIG. 5 is a perspective view of another exemplary embodiment of the present invention

In another embodiment, similar to the embodiment in FIG. 1A, illustrated in FIG. 5, a microanchor device 5 in an open configuration is illustrated having a first tissue engagement member and second tissue engagement member joined by a connector 12. Connector 12 in this embodiment is two coil springs made of a metal such as nitinol or stainless steel. The spacing between the coil springs can be changed to provide greater or lesser distance between the tissue engagement members. Multiple coil springs, such as two or three or more, may be used to provide different anchoring forces and angles to suit the different microanchor requirements of the anatomy.

Other embodiments contemplated include using a combination of the microanchor devices described herein by coupling one or more of microanchor devices 1-5, in any array or pattern, to any implantable device. In some embodiments, this plurality of varying anchoring devices, will extend along the length of the implantable device. The microanchor devices may be coupled to the implantable device in varying directions. The different angular placement of the microanchor devices will allow the individual microanchor devices to absorb forces from multiple directions when implanted into the body.

While particular embodiments of the present invention have been illustrated and described herein, the present invention should not be limited to such illustrations and descriptions. It should be apparent that changes and modifications may be incorporated and embodied as part of the present invention within the scope of the following claims.

EXAMPLE

A microanchor similar to that depicted in FIG. 1 was produced by first obtaining 0.018" diameter nitinol wire (Ft. Wayne Metals, Ft. Wayne, Ind.). A metal fixture was made having three rods mounted parallel to one another with a small gap therebetween. The nitinol wire was then wound in serpentine fashion around the three rods and secured such that the two ends of the wire wrapped completely around the outer two rods. Heat treatment of the serpentine shaped nitinol wire was accomplished by placing the fixture with the nitinol wire in a fluidized bed furnace at 480° C. for 7 minutes. The fixture having the nitinol wire was removed from the oven and quenched in water. After quenching, the nitinol wire was removed from the fixture. As a result of the thermal treatment, the wire retained its serpentine configuration. The outer loops were then trimmed to produce sharp points at a position approximately 200 degrees around the outer rods respectively.

The serpentine shaped nitinol wire was then preloaded by wrapping it around a single small diameter rod until it generally assumed the shape shown in FIG. 1A. A piece of suture was used to tie a quick-release knot at the crossover portion of the loaded nitinol wire.

Next, the trained and locked nitinol microanchor was evaluated for tissue retention performance. To simulate a stent frame, the locked microanchor was affixed to a small diameter rod. A piece of canine duodenum was used as the representative tissue. The microanchor was held against the tissue and the suture quick-release pulled to release the microanchor. The microanchor immediately unwound so that the two pincer ends of the microanchor anchor themselves into the tissue.

Load bearing performance of the anchored microanchor was determined by tying a string to the loop of the microanchor and vertically hanging a weight on the opposite end of this string. A starting weight of 20 gm was used. The weight was allowed to hang for approximately 5 minutes. If there were no signs of tissue tearing or the microanchor releasing, an additional 20 gm was added. This process was repeated until the weight reached 200 gm. With 200 gm hanging from the microanchor and after about 3 minutes the microanchor released itself from the tissue. There was no tearing of the tissue.

The invention claimed is:

1. A microanchor comprising:
a first tissue engagement member;
a second tissue engagement member;
a resilient, strain relieving connector joining said first tissue engagement member to said second tissue engagement member;
wherein said device has a retracted state and an engaged state, said first tissue engagement member and said second tissue engagement member farming a pincer in said engaged state;
wherein said first tissue engagement member and said second tissue engagement member are wound against tension in the retracted state, each of said first tissue engagement member and said second tissue engagement member curve in a first direction so that said first tissue engagement member and said second tissue engagement member are in close proximity to each other and in a second direction so that a first tip of said first tissue engagement member and a second tip of said second tissue engagement member point in opposing directions in the retracted state.

2. A microanchor as defined in claim 1, wherein said connector is elastic such that said device is reversibly deformable between said retracted state and said engaged state.

3. A microanchor as defined in claim 1, comprising stainless steel.

4. A microanchor as defined in claim 1, comprising nitinol.

5. A microanchor as defined in claim 1, wherein said first and second tissue engagement members in said engaged state are configured to penetrate tissue only about 1 mm.

6. A microanchor as defined in claim 1, further comprising a release line constraining said first and second tissue engagement members in said retracted state.

7. A microanchor as defined in claim 1, wherein said connector is a coiled spring.

8. A microanchor as defined in claim 1, wherein said first tissue engagement member and said connector comprises a substantially "S" shape when in said retracted state.

9. The microanchor of claim 1, wherein the first tissue engagement member and the second tissue engagement member overlap a plurality of times.

10. The microanchor of claim 1, wherein the connector is a coiled spring.

11. A method of anchoring a device to body tissue comprising:
attaching to the device at least one microanchor comprising:
a first tissue engagement member;
a second tissue engagement member;
a connector joining said first tissue engagement member to said second tissue engagement member;
wherein said device has a retracted state in which said first and second tissue engagement members are wound against tension in the connector and an engaged state, each of the said first tissue engagement member and said second tissue engagement curve in a first direction so that said first tissue engagement member and said second tissue engagement member are in close proximity to each other and in a second direction so that a first tip of said tissue engagement member and a second tip of said second tissue engagement member point in opposing directions;
a release line constraining said first and second tissue engagement members in said retracted state so that said first tissue engagement member and said second tissue engagement member are maintained in close proximity to each other by the release line;
endoluminally implanting the device with said device in said retracted state;
releasing said release line to convert said device into said engaged state, wherein said first tissue engagement member and said second tissue engagement member cooperate with tension in the connector to form a pincer in said engaged state.

12. The method of claim 11, wherein said anchor comprises stainless steel.

13. The method of claim 11, wherein said anchor comprises nitinol.

14. The method of claim 11, wherein said tissue engagement member is configured to penetrate tissue only about 1 mm.

15. A device having a microanchor, the microanchor comprising:
- a first tissue engagement member;
- a second tissue engagement member;
- a recoverable segment joining said first tissue engagement member to said second tissue engagement member;
- wherein said device has a retracted state and an engaged state;
- wherein said first tissue engagement member and said second tissue engagement member are wound against tension in the retracted state, each of said first tissue engagement member and said second tissue engagement member curve in a first direction so that said first tissue engagement member and said second tissue engagement member are in close proximity to each other and in a second direction so that a first tip of said tissue engagement member and a second tip of said second tissue engagement member point in opposing directions in the retracted state.

16. The device of claim 15 wherein the first tissue engagement member and the second tissue engagement member are maintained in the retracted state with a release line which couples the first tissue engagement member with the second tissue engagement member.

17. The device of claim 16 wherein the device is configured to move from the retracted state to the engaged state when the release line is released.

18. The device of claim 15 wherein tension is stored as potential energy in the recoverable segment in the retracted state.

19. The device of claim 15 wherein the device includes a plurality of microanchors coupled to the device in parallel.

20. The device of claim 15 wherein the device includes a plurality of microanchors coupled randomly in relation to each other.

21. The device of claim 15 wherein the first tissue engagement member forms an S-shaped curve with the recoverable segment.

22. The device of claim 15 wherein the first tissue engagement member and the second tissue engagement member form a pincer in the engaged state.

* * * * *